United States Patent [19]

Takanen et al.

[11] 4,079,030

[45] Mar. 14, 1978

[54] PRESSURE SENSITIVE ADHESIVE ACRYLIC ESTER POLYMER COMPOSITIONS EMPLOYING AT LEAST ONE DERIVATIVE OF A TETRAHYDRO-4H-1,3,5-OXADIAZINE-4-ONE AS A CROSS-LINKING AGENT

[75] Inventors: Lasse W. Takanen, Stockholm; Kjell Palmius; Gerard Myrthil, both of Spanga, all of Sweden

[73] Assignee: Salve S. A., Geneva, Switzerland

[21] Appl. No.: 623,965

[22] Filed: Oct. 20, 1975

[30] Foreign Application Priority Data

Oct. 22, 1974  Sweden .............................. 7413270

[51] Int. Cl.$^2$ ........................... C08K 5/05; C08K 5/00; C08F 18/00; C08C 19/22

[52] U.S. Cl. ................. 260/33.4 R; 156/331; 156/332; 260/79.5 C; 526/14; 526/15; 526/16; 526/50

[58] Field of Search ................. 526/50, 15, 16, 14, 526/79.5 C; 260/33.4 R

[56] References Cited

FOREIGN PATENT DOCUMENTS 1,204,819   9/1970   United Kingdom.

*Primary Examiner*—Herbert J. Lilling

[57] ABSTRACT

The invention relates to pressure sensitive adhesive compositions to be used in contact with the skin without causing contact eczema and allergies. Such a composition comprises an acrylic ester adhesive, at least one cross-linking agent such as tetrahydro-4H-1,3,5-oxadiazine-4-one or 5-alkyl-tetrahydro-s-triazine-2(1H)-one or -thione of the type specified below, and a catalyst.

13 Claims, No Drawings

PRESSURE SENSITIVE ADHESIVE ACRYLIC ESTER POLYMER COMPOSITIONS EMPLOYING AT LEAST ONE DERIVATIVE OF A TETRAHYDRO-4H-1,3,5-OXADIAZINE-4-ONE AS A CROSS-LINKING AGENT

The invention relates to pressure sensitive adhesives and more particularly, to increasing the cohesion of such adhesives.

The adhesive compounds referred to in the present application are pressure-sensitive adhesive agents, stable and tacky at normal temperature, for use on a flexible backing, preferably an adhesive plaster or strip in contact with the skin, which at the same time is suitable for use in securing and retaining objects to be used in autoclave sterilization, such as tubes, catheters, lids, etc., and which can also be removed from the skin or a surface at elevated temperature without the pressure-sensitive adhesive agent partially remaining. Such an adhesive agent contains, for instance, 99.5 – 90 percent by weight of a copolymerisate of one or more monomeric alkyl acrylates, the alkyl group containing 2 – 10 carbon atoms, or a mixture of 95 – 80 percent by weight acrylic esters and 5 – 20 percent by weight vinyl acetate or vinyl propionate. Such an adhesive compound also suitably includes 0.5 – 10 percent by weight 2-hydroxyethyl or 2-hydroxypropyl methacrylate or 2-hydroxyethyl or 2-hydroxypropyl acrylate or a mixture of these in a solvent consisting of easily volative esters such as methyl or ethyl acetate, aliphatic, cycloaliphatic or aromatic hydrocarbons or a mixture of these. Typical examples of the use of such adhesive agents are for adhesive plasters, dressings provided with a compress, foot plasters for corns, for instance, self-adhesive compresses, operation cloths, etc.

It is known that pressure-sensitive adhesive strips can be manufactured from copolymers consisting of acrylic esters and methacrylic esters or non-tertiary alcohols with 1 – 14 carbon atoms. It is also known that these polymers are too soft and lack cohesion (internal strength), which causes remnants of adhesive compound to remain when the strip is removed, and also causes the strip to slip and be displaced from the application point if there is constant tension.

Numerous attempts have been made to increase the cohesion of such adhesive compounds, for instance by adding peroxides after the polymerisation and producing meshing at elevated temperature. However, such compounds age quickly since the meshing continues at room temperature. Meshing, with resultant increase in cohesion of the adhesive compound, can also be achieved by adding polyfunctional organic compounds having at least two functional groups in the molecule. The copolymer may include, for instance, reactive carboxyl or hydroxyl groups which are then subjected to curing (meshing) by the addition of, for instance, 2 or more functional compounds such as isocyanates. These substances, however, even in small quantities cause contact eczema on the skin and it is obvious that such substances should be avoided, particularly in adhesive compounds coming into contact with the skin.

It is known that a meshing reaction (cross-linking) between hydroxyl groups in a polymer and compounds containing two or more N-α-alkylol or N-α-alkoxy methyl groups can occur. These reactions have frequently been used in the varnish and paint industry as well as the textile industry where the hydroxyl groups in cotton and reclaimed cellulose are enmeshed with the above-mentioned compounds, thus enabling the production of crease-resistant textiles.

Both high and low reactive compounds have been used for these purposes.

High reactive compounds which may be used include bis-(hydroxymethyl) urea, bis-(methoxymethyl) urea, 1,3-bis-(hydroxymethyl)-and 1,3-bis-(methoxymethyl)-derivative of imidazolidine-2-on and 1,3-bis-(hydroxymethyl)- and 1,3-bis-(methoxymethyl) derivative of tetrahydropyrimidine-2-on.

The stability against hydrolysis of an N-α-alkoxymethyl compound or cross-linking in a polymer where the cross-linking (meshing) is effected by N-α-alkylol or N-α-alkoxymethyl compounds is dependent on the stability of the carbon-oxygen and nitrogen-carbon bond:

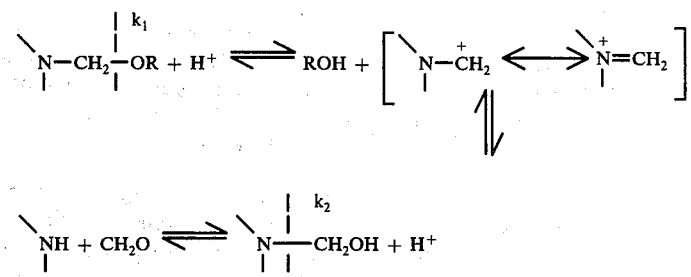

The constant $k_1$ of the hydrolysis rate is at the same time a measure of the reactivity of the N-α-alkoxymethyl (N-α-alkylol) compound. Compounds having high reactivity (high $k_1$ value) also have a higher $k_2$ value (ability to split formaldehyde) than compounds with lower reactivity. $k_1$ and $k_2$ are thus proportional in a compound in a fixed relationship to one another in a given compound.

When the N-C-link is split formaldehyde is released. Since even in small quantities formaldehyde may cause contact eczema and allergies in contact with the skin, compound having high reactivity should not be used to achieve meshing of the adhesive compound.

If in an adhesive compound consisting of a polymerisate containing hydroxyl groups cross-linking is effected with compounds containing two or more N-α-alkylol or N-α-alkoxymethyl groups, the presence of formaldehyde in the adhesive compound can be shown in the following manner. A strip 1 × 3 cm of a flexible carrier on which has been applied 40 – 50 g/m² adhesive compound which has been meshed with the N-α-methylol or N-α-methoxy methyl compound to be examined and which has been stored for a certain period, is placed in a weighing glass provided with a lid. A small open beaker is also placed on the weighing dish, said beaker containing 2 ml of a solution of chromatropa acid (1 g chromatropa acid dissolved in 250 ml concentrated sulphuric acid). The complete arrangement is closed with a lid and allowed to stand at room temperature for 24 hours. A colourless or very faintly voilet coloured chromatropa acid solution indicates a content of 10 ppm or less of formaldehyde in the adhesive compound. An intense violet colour indicates that the formaldehyde content exceeds 100 ppm.

Another drawback with high reactive resins of the type mentioned above is that cross-linking and gelling of the adhesive compound solution takes place too early which makes it impossible to coat the compound on a flexible carrier.

Melamine-formaldehyde resins can be used as cross-linking agents, but it has been found that N-α-alkylol (for example N-α-methylol) groups in these are unstable, formation of formaldehyde occurring. The reaction products between 1 mol melamine and up to 4 moles formaldehyde, which have then been esterified with alcohols are often difficult to purify and containing considerable quantities of formaldehyde. Furthermore, trimethylol and higher methylolated melamine derivative and corresponding compounds esterified with alcohols may react and become polymerised because of the three or more reactive groups and free NH groups. The adhesive compounds may therefore age and lose their stickiness if stored too long.

N-α-alkylol and N-α-alkoxymethyl compounds having low reactivity, such as 1,3-bis(hydroxymethyl)- and 1,3-bis-(alkoxymethyl) derivative of imidazolidin 2-on, which are further substituted by hydroxyl groups in positions 4 and 5 and, for example, compounds such as 1,3-bis-(hydroxymethyl)-4-methoxy-5,5-dimethyl-tetrahydropyrimidine-4-on and corresponding 1,3-bis-(alkoxymethyl) derivatives. if a meshing reaction is to occur (to increase the internal cohesion of the compound and ability even at higher temperatures not to leave remnants on the recipient surface), require either heating after removal of the solvent to such high temperatures that, for instance, thermoplastic backing softens and cannot be handled in a coating machine, or impractically long curing times at lower temperatures.

The present invention provides a pressure sensitive adhesive composition comprising 1. an acrylic ester adhesive including the molecular grouping

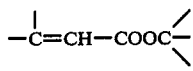

2. a cross-linking agent which is at least one tetrahydro-4H-1,3,5-oxadiazine-4-one of formula

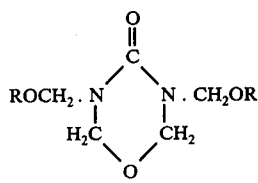

where R is an alkyl group with straight hydrocarbon chain containing 1 − 4 carbon atoms, or 5-alkyl-tetrahydro-s-triazine-2(1H)-one or -thione of the formula

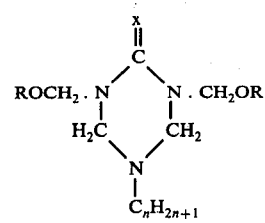

where $n = 1 - 5$ and R = H or an alkyl group with a straight hydrocarbon chain containing 1 − 4 carbon atoms and where $x$ is oxygen or sulphur, or a mixture thereof and 3. a catalyst.

In a preferred embodiment of the invention, the cross-linking agent is present in an amount of 0.1 − 2.0 percent by weight based on the weight of the composition.

The catalyst may be an inorganic acid such as hydrochloric acid or sulphuric acid, an organic acid such as toluene sulphonic acid or methane sulphonic acid or a Lewis acid such as boron trifluoride e.g. in a quantity of 0.01 − 0.5% calculated on the weight of the acrylic ester. Catalyst 1010 marketed by American Cyanamid may also be used as catalyst.

The composition of the invention shows cohesion of the adhesive compound through cross-linking when a substrate coated with the adhesive composition is removed from the skin or a surface, even at elevated temperature, no remnants of adhesive remain on the skin or surface.

After storage testing, it has been ascertained that the above-mentioned cross-linking agent does not split to form formaldehyde which, is a great advantage, particularly in the case of products to be used in contact with the skin, as formaldehyde can cause contact eczema and allergies.

In accordance with a further feature of the invention, there is provided an adhesive sticker or plaster comprising a flexible plastics material, at least one bonding surface of which is coated with a composition according to the invention.

Thermoplastic foils such as PVC which are often used as backing for plasters, easily polar solvents, thus becoming soft and difficult, if not impossible to handle. It is therefore advantageous if the adhesive compounds are soluble in a mixture containing up to 80% hexane or heptane or 85% cyclohexane or aromatic solvent and only 15 − 20% polar solvent such as methyl or ethyl acetate or lower aliphatic ketones such as acetone and methylethylketone.

The cross-linking agent used in the invention can be mixed into the acrylic polymer solution without meshing or gelling occurring in the solution during a storage time of over 6 months at room temperature. Even when the acid catalyst has been added, the polymer solution can be kept for several months by the addition of alcohols, preferably readily volatile aliphatic alcohols such as methyl, ethyl, n-propyl or isopropyl alcohol in a quantity of 0.5 to 5 percent by weight and more, calculated on the weight of the polymer so that such meshing and gelling of the polymer solution is prevented. The solution can then be coated on the flexible backing by ordinary coating methods e.g. using blades or rollers.

The cross-linking inhibiting effect of the solvent can be removed, however, and cross-linking made to occur at low heat from 50°– 75° C over a short period of 5 – 15 minutes after the solvent has evaporated. This is a great advantage when coating thermoplastic foils, for instance, which soften at temperatures over 75° C.

The following Examples are given to illustrate the invention. Temperatures are in ° C.

EXAMPLE 1

19.4 g vinyl acetate
31.5 g n-butylacrylate
46.8 g 2-ethylhexylacrylate
2.3 g 2-hydroxyethylmethacrylate The above constituents were dissolved in 31 g ethylacetate and 47 g cyclohexane; 0.25 g benzoylperoxide was added. One quarter of this solution was placed in a reaction vessel with reflux coolers and heated to 78°. 30 minutes after this temperature had been reached, the rest of the solution was added over a period of 4 hours. The temperature was maintained at 82°– 85° during the rest of the polymerisation process which was permitted to continue for a total of 12 hours.

0.13 g 3,5-bis(methoxymethyl)-tetrahydro-4H-1,3,5-oxadiazine-4-one dissolved in 5 g methanol and 0.05 g p-toluene sulphonic acid dissolved in 5 g methanol were added to the polymer solution and mixed well.

A strip consisting of a plasticized PVC foil having a weight of 95 g/m$^2$ was coated with an adhesive compound manufactured in accordance with Example 1. The solvent evaporated and the strip was kept at a temperature of 65° for 6 minutes. The weight of the adhesive coating was 32 g/m$^2$.

By adhesion ability is meant the force required to remove an adhesive strip having a width of 25 mm an angle of 180° from a polished steel surface. The test was performed in accordance with "Test Methods for Pressure Sensitive Tapes," Pressure Sensitive Tape Council Glennview, Illinois, method PSTC-1:180° peel adhesion. The test was performed at room temperature.

The above-mentioned adhesive strip had an adhesion ability of 840 g/25 mm.

The adhesive strip had satisfactory adhesion ability on the skin and could be removed after 24 hours without remnants of the adhesive compound being left on the skin.

No formaldehyde content could be found in the adhesive compound, which was tested as described above.

The adhesive strip could be removed from a steel plate heated to 70° without leaving remnants.

EXAMPLE 2

92.0 g n-butyl acrylate
8.0 g 2-hydroxy ethyl methacrylate

The above constituents were dissolved in a mixture of 30 g ethyl acetate and 35 g cyclohexane. 1.0 g benzoyl peroxide was added and the solution polymerized in the same manner as in Example 1. However, 5 hours after the start of polymerisation 0.2 g benzoyl peroxide and thereafter during polymerisation a further mixture of 10 g toluene and 110 g benzine (boiling point range 80°– 110° were added. The polymerisation was permitted to continue for 10 hours.

0.7 g 3.5-bis-(ethoxy methyl)-tetrahydro-4H-1,3,5-oxadiazine-4-one dissolved in 8 ml methanol and 0.02 g boron trifluoride (as a 42% solution in diethyl ether) in 10 ml methanol were then added to the polymer solution.

A strip consisting of taffeta manufacture from cellulose acetate fibre and having a weight of 80 g/m$^2$ was coated with the adhesive compound manufactured in accordance with Example 2. The solvent evaporated and the strip was kept at a temperature of 65° for 6 minutes. The weight of the adhesive coating was 60 g/m$^2$.

The adhesive strip had an adhesion ability of 1060 g/25 mm. It adhered well to the skin and could be removed without trace after 24 hours.

The adhesive strip could be removed from a steel plate heated to 120° without leaving traces.

No formaldehyde content could be found after 7 months storage, the tests being performed in accordance with the method described above.

EXAMPLE 3

19.2 g vinyl acetate
32.5 g n-butyl acrylate
47.4 g 2-ethyl hexyl acrylate
0.9 g 2-hydroxy ethyl methacrylate The above constituents were mixed with 35 g ethyl acetate, 60 g cyclohexane and 0.8 benzoyl peroxide and polymerised in the manner described in Example 1. 6 hours after the polymerisation had started 120 g benzene (boiling point interval 80°– 110°) were added while polymerisation was in progress.

1.0 g 3,5-bis-(ethoxy methyl)-tetrahydro-4H-1,3,5-oxadiazine-4-one dissolved in 8 ml methanol and 0.5 g catalyst 1010 from American Cyanamide dissolved in 2.7 ml methanol were then added to the polymer solution and mixed well.

A backing material consisting of a strip of non-woven material, type V29965, manufacturer Carl Freudenberg, having a thickness of 75 my and a further weight of 50 g/m$^2$, was coated with the adhesive compound manufactured in accordance with Example 3.

The solvent was evaporated and the strip kept at a temperature of 55° for 12 minutes. The weight of the adhesive coating was 43 g/m$^2$.

The adhesive strip had an adhesion ability of 770 g/25 mm. It had good adhesion ability on the skin and could be removed without traces after 48 hours.

The adhesive strip could be removed from a steel plate heated to 70° without leaving any traces.

No formaldehyde could be found after a storage time of 1 month at 38° and 90% relative humidity, the tests being performed as described above.

EXAMPLE 4

11.0 g vinyl propionate
39.9 g n-butyl acrylate
46.0 g 2-ethyl hexyl acrylate
3.1 g 2-hydroxy propyl acrylate The above constituents were mixed with 20 g ethylacetate and 10 g benzene (boiling point interval 80°– 110°), 0.40 g benzoyl peroxide was added and the solution polymerised in the same manner as in Example 1 for 8 hours. 5 hours after the start of polymerisation another 125 g benzene (boiling point interval 80° – 110°) were added in small portions.

1.4 g 3.5-bis-(n-butoxymethyl)-tetrahydro-4H-1,3,5-oxadiazine-4-one dissolved in 1 ml n-propanol and 0.04 g methane sulphonic acid dissolved in 1 ml methanol were then added to the polymer solution.

A strip consisting of taffeta, as in Example 2, was coated with adhesive compound in accordance with Example 4. The solvent was evaporated and the strip kept at 75° for 12 minutes. The weight of the adhesive coating was 56 g/m².

The adhesive strip had an adhesion ability of 910 g/25 mm.

Otherwise the adhesive strip had the same properties as that manufactured in accordance with Example 2.

EXAMPLE 5

To a solution manufactured in accordance with Example 1 and containing 100 g dry polymer were added 0.35 g 5-methyl-1,3-bis-(hydroxymethyl)-tetrahydro-s-triazine-2(1H)-one dissolved in 1,5 ml ethanol and 0.07 g paratoluene sulphonic acid dissolved in 2 ml ethanol.

A strip consisting of plasticized PVC foil in accordance with Example 1 was coated with the adhesive compound manufactured according to Example 5.

After the solvent had evaporated, the strip was kept at 53° for 14 minutes. The weight of the adhesive coating was 28 g/m².

The adhesive strip had an adhesion ability of 1175 g/25 mm and otherwise the same properties as that manufactured in accordance with Example 1.

EXAMPLE 6

To a solution manufactured in accordance with Example 1 and containing 100 g dry polymer were added 0.7 g 5-n-butyl-1,3-bis-(n-butoxymethyl)-tetrahydro-s-triazine-2(1H)-one dissolved in 2.5 g isopropanol and 0.5 g catalyst 1010 from American Cyanamide dissolved in 2 ml methanol.

A strip consisting of plasticized PVC foil in accordance with Example 1 was coated with the adhesive compound manufactured in accordance with Example 6. After the solvent had evaporated, the strip was kept at 66° for 15 minutes. The weight of the adhesive coating was 36 g/m².

The adhesive strip had an adhesion ability of 1130 g/m² and otherwise the same properties as that manufactured in accordance with Example 1.

What we claim is:

1. A pressure sensitive, adhesive composition comprising
   1. a polymer selected from the group consisting of (a) 99.5 – 90% by weight of at least one alkyl acrylate, the alkyl group containing 2 – 10 carbon atoms, and 0.5 – 10% by weight of a monomer selected from the group consisting of 2-hydroxyethyl methacrylate, 2-hydroxypropyl methacrylate, 2-hydroxyethyl acrylate and 2-hydroxypropyl acrylate; and (b) 95 – 78.3% by weight of at least one alkyl acrylate, the alkyl group containing 2–10 carbon atoms, 5 – 20% by weight of a vinyl compound selected from the group consisting of vinyl acetate and vinyl propionate and 0.5 – 10% by weight of a monomer selected from the group consisting of 2-hydroxyethyl methacrylate, 2-hydroxypropyl methacrylate, 2-hydroxyethyl acrylate and 2-hydroxypropyl acrylate;
   2. a cross-linking agent which is at least one tetrahydro-4H-1,3,5-oxadiazine-4-one of formula

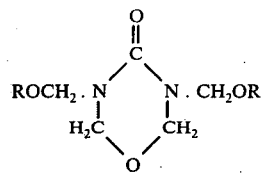

where R is an alkyl group with straight hydrocarbon chain containing 1 – 4 carbon atoms; and
   3. a catalyst selected from the group consisting of inorganic acids, organic acids and Lewis acids.

2. Composition according to claim 1, wherein the cross-linking agent is present in an amount of 0.1 – 2.0 percent by weight of the composition.

3. Composition according to claim 1, wherein the acid is hydrochloric or sulphuric acid toluene sulphonic acid or methane sulphonic acid or boron trifluoride.

4. Composition according to claim 1, wherein the acid is present in an amount of 0.01 – 0.5% calculated on the weight of the acrylic ester.

5. Composition according to claim 1, including a solvent to inhibit crosslinking.

6. Composition according to claim 5, wherein the solvent is an alcohol.

7. Composition according to claim 6, wherein the alcohol is methanol, ethanol, n-propanol or iso-propanol.

8. Composition according to claim 5, wherein the solvent is present in an amount of at least 0.5% by weight based on the weight of the acrylic ester.

9. Composition according to claim 8, containing 0.5 – 5% by weight of solvent.

10. Composition according to claim 1 wherein the crosslinking agent is 3,5-bis-(methoxymethyl)-tetrahydro-4H-1,3,5-oxadiazine-4-one
3,5-bis-(ethoxymethyl)-tetrahydro-4H-1,3,5-oxadiazine-41-one,
3,5-bis-(n-butoxymethyl)-tetrahydro-4H-1,3,5-oxadiazine-4-one.

11. Composition according to claim 1 wherein the cross-linking agent is 3,5-bis-(ethoxymethyl)-tetrahydro-4H-1,3,5-oxadizine-4-one.

12. Composition according to claim 1 wherein the cross-linking agent is 3,5-bis-(n-butoxymethyl)-tetrahydro-4H-1,3,5-oxadiazine-4-one.

13. Method of increasing the cohesion of an acrylic ester based polymer-containing pressure-sensitive adhesive comprises combining
   1. a polymer selected from the group consisting of (a) 99.5 – 90% by weight of at least one alkyl acrylate, the alkyl group containing 2 – 10 carbon atoms, and 0.5 – 10% by weight of a monomer selected from the group consisting of 2-hydroxyethyl methacrylate, 2-hydroxypropyl methacrylate, 2-hydroxyethyl acrylate and 2-hydroxypropyl acrylate; and (b) 95 – 78.3% by weight of at least one alkyl acrylate, the alkyl group containing 2 – 10 carbon atoms, 5 – 20% by weight of a vinyl compound selected from the group consisting of vinyl acetate and vinyl propionate and 0.5 – 10% by weight of a monomer selected from the group consisting of 2-hydroxyethyl methacrylate, 2-hydroxypropyl methacrylate, 2-hydroxyethyl acrylate and 2-hydroxypropyl acrylate; with 2. a cross-linking agent which is at least one tetrahydro-4H-1,3,5-oxadiazine-4-one of formula
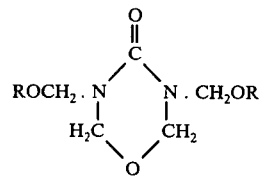
where R is an alkyl group with straight hydrocarbon chain containing 1 – 4 carbon atoms; and
3. a catalyst selected from the group consisting of inorganic acids, organic acids and Lewis acids.
* * * * *